United States Patent [19]

Sartinoranont

[11] 4,447,222

[45] May 8, 1984

[54] TAMPON INSERTER

[76] Inventor: Sarnt Sartinoranont, Rte. 1, Box 758, Starke, Fla. 32091

[21] Appl. No.: 289,398

[22] Filed: Aug. 3, 1981

[51] Int. Cl.³ .......................................... A61M 31/00
[52] U.S. Cl. ..................................................... 604/15
[58] Field of Search ............... 128/225, 263, 264, 270, 128/284, 285, 130; 604/327, 904, 11-18

[56] References Cited

U.S. PATENT DOCUMENTS 3,590,816 7/1971 Rosenthal ........................... 128/130
3,753,437 8/1973 Hood et al. .......................... 128/263

FOREIGN PATENT DOCUMENTS 2265416 10/1975 France ................................ 128/263

Primary Examiner—Benjamin R. Padgett
Assistant Examiner—T. J. Wallen
Attorney, Agent, or Firm—Arthur G. Yeager

[57] ABSTRACT

A device for inserting a sterile tampon comprising an outer tube, an insertion tube which slides telescopically inside the outer tube, and a sterile tampon releasably attached to the forward end of the insertion tube and pressed against the inside of the closed forward end of the outer tube, the outer tube being weakened at its forward end so as to rupture when manual pressure is applied to the insertion tube to permit ejection of the tampon into the vagina, the outer tube having two spaced laterally outwardly projecting members, one located adjacent the rearward end of the outer tube and the other located in the central portion between the forward end and the rearward end of the outer tube to position the forward end of the outer tube at a desired depth, the member at the rearward end of the outer tube serving as a finger grip, the insertion tube having at its forward end a means for releasably gripping the string end of the tampon and at its rearward end a laterally outwardly projecting member to prevent sliding of the insertion tube into the outer tube beyond the position where the projecting member contacts the rearward end of the outer tube.

12 Claims, 7 Drawing Figures

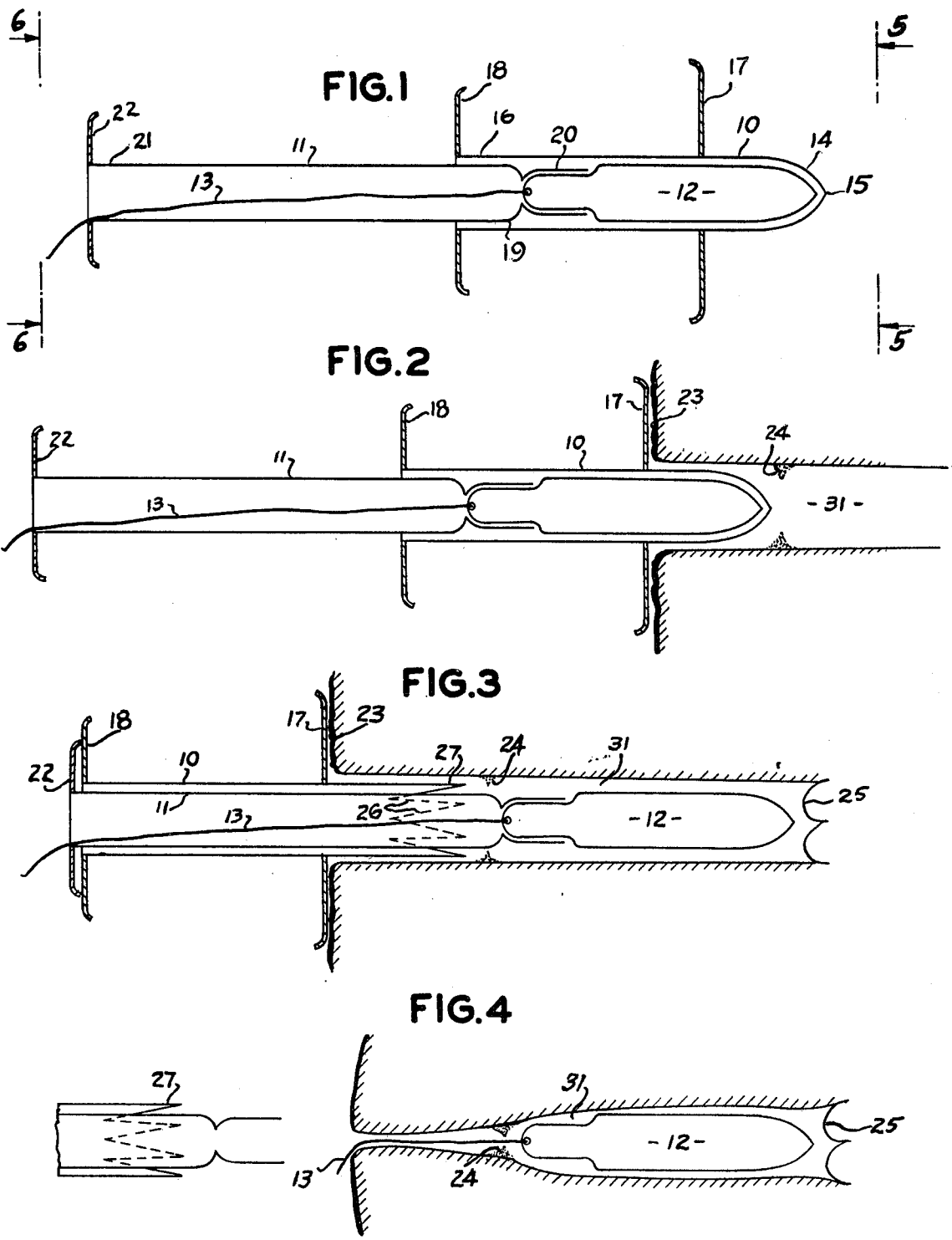

U.S. Patent  May 8, 1984  Sheet 2 of 2  4,447,222
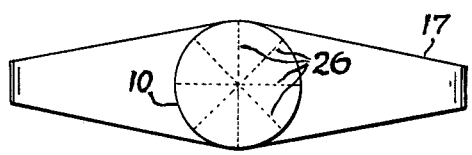
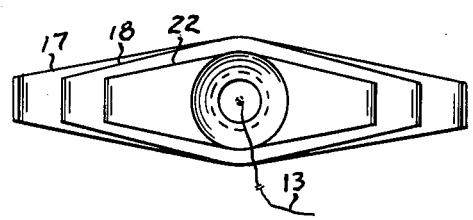
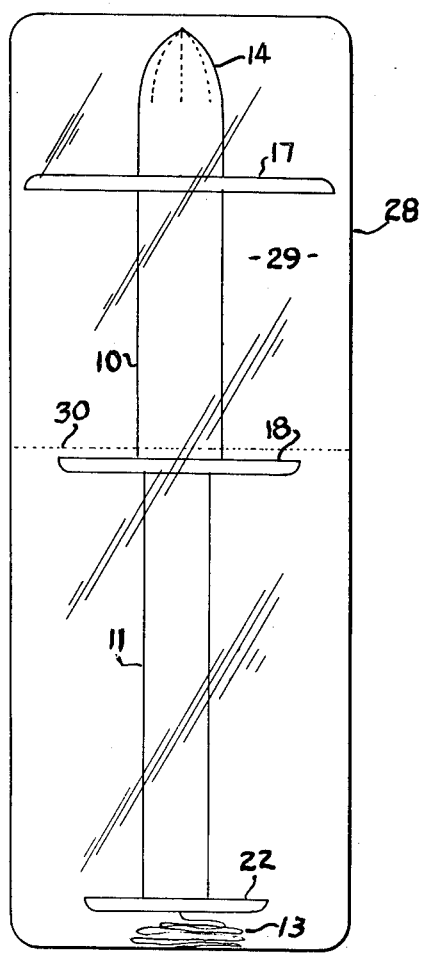

TAMPON INSERTER

BACKGROUND OF THE INVENTION

The use of tampons by women to absorb the menstrual discharge has increased dramatically in the past several years, but at the same time there has been a sharp increase in vaginal infections and diseases which have been attributed to the use of tampons. Among the vaginal disorders and diseases are vaginal ulcers, vaginitis, pelvic inflammatory disease, and, most recently, toxic shock syndrome. Studies of toxic shock syndrome have led to the conclusion that this is a very dangerous infection, probably caused by contamination of the tampon before or during the insertion of the tampon. Normal flora bacteria on the skin can, when introduced into the vagina during menstruation, become pathogenic. The bloody discharge concentrates in the tampon in the vagina, the vagina serving as an incubator for any bacteria and enhancing the rapid growth of the bacteria to cause infection. It is believed that toxic shock syndrome is the result of introducing *Staphylcoccus aureus* into the vagina with the tampon and then permitting these bacteria to multiply to produce toxin and cause a serious illness.

It is obvious that the handling of the tampon and its insertion without the benefit of a sterile device is readily susceptible to contamination by any bacteria on the hands and labia. While there have been many recent designs of devices for inserting tampons, none of these has provided a means for insuring that the tampon remains sterile until insertion into the vagina. Furthermore the previous devices have not provided a means for insuring that the inserter is positioned properly so as to eject the tampon into the proper location into the vagina.

It is an object of this invention to provide a new and improved tampon inserter. It is another object of this invention to provide a tampon inserter which will deliver a sterilized tampon. It is another object of this invention to provide a tampon inserter which is properly positioned to insert the tampon to its proper placement. Other objects will appear from a more detailed description of this invention which follows.

BRIEF SUMMARY OF THE INVENTION

This invention provides a device for inserting a sterile tampon into a vagina, comprising an elongated outer tube having a forward end and a rearward end, an elongated insertion tube telescopically slideable within said outer tube and having a front end and a back end, and a sterile tampon engageable by said front end of said insertion tube, said outer tube having two spaced laterally outwardly projecting members, the first of said members being located adjacent said rearward end and the second of said members being located generally spaced rearwardly from said forward end, said second member being engageable with the labia so as to prevent insertion of said forward end into the vagina beyond the general location of the hymen remnant; said insertion tube having a laterally outwardly projecting third member to prevent sliding of said insertion tube into said outer tube beyond the position where said tampon is disposed between the hymen remnant and the cervix when said first member engages the labia. In preferred embodiments of this invention the two tubes are cylindrical, the forward end of the outer tube is a rounded, tapered shape with lines of weakness extending longitudinally rearward from the apex of the shape, the forward end of the insertion tube is cup-shaped and adapted to fit around the string end of the tampon and the insertion tube is longer than the outer tube. Another embodiment of this invention comprises an easily openable package containing the assembled device for inserting a sterile tampon, the package comprising a plastic film envelope enclosing the device in sterile condition and having means for easily opening the package manually to provide access for removing the entire device from the package and inserting a sterile tampon into the vagina without contaminating the device or tampon before insertion.

BRIEF DESCRIPTION OF THE DRAWINGS

The novel features believed to be characteristic of this invention are set forth with particularity in the appended claims. The invention, itself, however, both as to its organization and method of operation, together with further objects and advantages thereof, may best be understood by reference to the following description taken in connection with the accompanying drawings in which:

FIG. 1 is a side elevational view of the device of this invention.

FIG. 2 is a side view illustrating the device of this invention being inserted into a vagina.

FIG. 3 is a side view illustrating the ejection of the tampon into the vagina from the device of this invention.

FIG. 4 is a side view illustrating the device of this invention after withdrawal from the vagina and leaving the tampon in the vagina.

FIG. 5 is an end view at the forward end of the device of this invention as shown and indicated at 5—5 of FIG. 1.

FIG. 6 is an end view of the rearward end of the device of this invention as indicated at 6—6 of FIG. 1.

FIG. 7 is an overhead plan view of a package containing the device of this invention.

DETAILED DESCRIPTION OF THE INVENTION

The features of the device of this invention can best be understood by reference to FIGS. 1, 5, and 6. The device comprises three separate items; namely, outer tube 10, insertion tube 11, and tampon 12 with removal string 13 attached thereto. Sterile tampon 12 is located inside outer tube 10 at its forward end which is closed to the outside surrounding atmosphere. The rearward end of tampon 12 is held in a releasable gripping means 20 on front end 19 of insertion tube 11. The gripping means may be any convenient means to hold the rearward end of tampon 12 firmly, and to transmit the manual pressure applied to insertion tube 11 that will cause forward end 14 of outer tube 10 to rupture and to permit ejection of tampon 12 from outer tube 10 into the vagina, as will be more completely described later. In this instance the gripping means 20 on front end 19 of insertion tube 11 is shown as a cup-shaped recess fitting around the rearward end of tampon 12.

Insertion tube 11 is of a suitable size to be telescopically slideable into outer tube 10 through rearward end 16. String 13 extends from tampon 12 through the central hollow space of insertion 11 to back end 21.

Three laterally outwardly projecting members 17, 18, and 22 are positioned to operate the device of this invention properly. First member 17 is located generally in the central portion of outer tube 10 between forward end 14 and rearward end 16. The purpose of member 17 is to properly position forward end 14 when the device is inserted into the vagina and member 17 engages the labia. For this purpose member 17 is located such that the axial distance from apex 15 to first member 17 is about one-third of the total overall length of outer tube 10. Second member 18 is located at rearward end 16 of outer tube 10 and serves as a finger grip for holding outer tube 10 in position while pressing insertion tube 11 inwardly into outer tube 10 in the operation to eject tampon 12 therefrom. Third member 22 is located at back end 21 of insertion tube 11 and serves as a convenient handle for pressing insertion tube 11 inwardly of outer tube 10, and also serves as a stop to prevent movement of insertion tube 11 inwardly any farther than the position reached when member 22 contacts rearward end 16 of outer tube 10. It is not critical that members 17,18, and 22 have any special design although the preferred embodiment is shown in FIG. 6 wherein each member comprises two thin, flat arms, diametrically opposed to each other.

Forward end 14 of outer tube 10 is fully enclosed around the forward end of tampon 12 and yet it contains weakened areas to permit the rupture of forward end 14 when manual pressure is applied to the tampon inside of outer tube 10 so that tampon 12 may be ejected therefrom. In the preferred embodiment forward end 14 is rounded, tapered shape and lines of weakness 26 extend from apex 15 longitudinally rearward at least to the nontapering portion of outer tube 10.

The operation and use of the device of this invention is best illustrated in FIGS. 2-4. The device of this invention as shown in FIG. 1 is illustrated in FIG. 2 being inserted into the vagina 31. Member 17 is positioned approximately 1 inch to the rear of apex 15 so as to provide a convenient positioning means engagable with labia 23 to prevent forward end 14 of outer tube 10 from being inserted into the vagina beyond the hymen remnant 24, which is the junction between the skin of the labia 23 and the mucous membrane of the vagina 31.

With the device inserted as shown in FIG. 2 tampon 12 is then ejected from the device into the vagina 31 as shown in FIG. 3. Manual pressure is applied to member 22 to cause insertion tube 11 to slide telescopically into outer tube 10, which in turn causes tampon 12 to press against the inside of forward end 14 and to rupture that end along the lines of weakness 26. Insertion tube 11 is then moved as far forward as possible, which is the position shown in FIG. 3 when third member 22 comes in contact with second member 18. The lines of weakness 26 as shown in FIG. 5 are ruptured and the individual triangular segments open to the position shown in FIG. 3 and permit insertion tube 11 to be moved to its full forward position as shown in FIG. 3. In this position tampon 12 is inserted in the vagina 31 at its proper location just short of cervix 25. The combination of outer tube 10 and insertion tube 11 in the position shown in FIG. 3 is then withdrawn from the vagina leaving tampon 12 in place with string 13 available outside of labia 23 for eventual removal of tampon 12.

It may be appreciated that the cross sectional shape of tubes 10 and 11 may be of any convenient form, the most appropriate being circular so that these tubes are cylindrical. It is also appropriate to make tubes 10 and 11 from an inexpensive plastic material which can be sterilized and which is inexpensive enough to be thrown away after a single use.

In FIG. 7 there is shown a package of the sterilized device of this invention as it might be marketed and handled before use of the tampon inserts. It is only necessary that the device be encased in a plastic film 29 which is air tight and thus will maintain the previously sterilized condition of the packaged device. The package should be easily opened by means of a weakened area or a tear strip along the general line 30 which will permit removal of the device from the package by handling insertion tube 11 without the necessity of touching first member 17 or forward end 14 of outer tube 10, which could cause contamination and infection of the vagina, if it were not maintained in its sterile condition. A preferred package is one having a stiff backing 28 on which the device rests with members 17,18, and 22 positioned parallel to backing 28, and a transparent plastic film 29 sealed to backing 28 and completely covering the device of this invention to produce a flat package. A weakened line 30 is one which can be readily opened manually to permit the insertion tube 11 to be gripped by fingers so as to remove the entire device from the package without touching first member 17 or any part of forward end 14, which otherwise might contaminate the sterile forward end 14 and tampon 12 before it is inserted into the vagina.

Even if forward end 14 is contaminated by being touched by the fingers or the labia, tampon 12 will remain sterile so long as lines of weakness 26 have not been ruptured. Accordingly, a sterile tampon 12 could still be inserted into the vagina since forward end 14 of outer tube 10 does not reach beyond hymen remnant 24.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A device for inserting a sterile tampon into a human vagina comprising an elongated outer tube having forward and rearward opposite ends, an elongated hollow insertion tube telescopically slideable within said outer tube and having an open back end, a sterile tampon engageable by said front end of said insertion tube, said outer tube having two spaced laterally outwardly projecting members, the first of said members being fixedly located generally spaced rearwardly from said forward end and being engageable with the labia so as to prevent insertion of said forward end into the vagina beyond the general location of the hymen remnant, and the second of said members being located adjacent said rearward end, said insertion tube having a laterally outwardly projecting third member to prevent sliding of said insertion tube into said outer tube beyond the position where said tampon is disposed between the hymen remnant and the cervix when said first member engages the labia, said insertion tube with said third member engaging said second member having said front end projecting outwardly from said outer tube to forcibly eject said tampon from said outer tube into its position between the hymen remnant and the cervix.

2. The device of claim 1 wherein said outer tube and said insertion tube are cylindrical.

3. The device of claim 1 wherein said forward end is a rounded, tapered shape with lines of weakness in the wall of said outer tube extending longitudinally rearward from the apex of said shape.

4. The device of claim 3 wherein said lines of weakness are rupturable by manual pressure applied from said back end to permit ejection of said tampon through said forward end.

5. The device of claim 1 wherein said laterally projecting members each comprise a pair of arms projecting outwardly from diametrically opposite sides of the tube to which the respective member is attached.

6. The device of claim 1 wherein said sterile tampon is releasably attached to said front end.

7. The device of claim 6 wherein said front end is cup-shaped and adapted to fit around the string end of said tampon.

8. The device of claim 1 wherein said sterile tampon is pressed against the inside of said forward end.

9. The device of claim 1 wherein said first member is spaced about twice as far from said second member as it is spaced from said forward end.

10. The device of claim 1 wherein said first member projects outwardly farther than said second member, and said second member projects outwardly farther than said third member.

11. An easily openable package combination comprising a device for inserting a sterile tampon into a human vagina comprising an elongated outer tube having forward and rearward opposite ends, an elongated hollow insertion tube telescopically slideable within said outer tube and having an open front end and an open back end, a sterile tampon engageable by said front end of said insertion tube, said outer tube having two spaced laterally outwardly projecting members, the first of said members being fixedly located generally spaced rearwardly from said forward end and being engageable with the labia so as to prevent insertion of said forward end into the vagina beyond the general location of the hymen remnant, and the second of said members being located adjacent said rearward end, said insertion tube having a laterally outwardly projecting third member to prevent sliding of said insertion tube into said outer tube beyond the position where said tampon is disposed between the hymen remnant and the cervix when said first member engages the labia, said insertion tube with said third member engaging said second member having said front end projecting outwardly from said outer tube to forcibly eject said tampon from said outer tube into its position between the hymen remnant and the cervix, said package including a plastic film envelope enclosing said device in sterile condition, means for readily opening said package manually to provide access for gripping said device rearwardly of said first member and removing said device from said package and inserting said device into the human vagina without contacting the remaining sterile portions of said device with bacterial contamination before insertion thereof and ejection of said tampon therefrom into its location between the hymen remnant and the cervix.

12. The package of claim 11 wherein said device is held tightly against a stiff backing member by a transparent plastic film stretched over said device and said backing member to produce an air tight and sterile enclosure around said device, said first, second, and third members are positioned generally parallel to each other and to said backing member to produce a substantially flat package with the shortest dimension being the outside dimension of said outer tube and the thickness of said backing member.

* * * * *